United States Patent [19]
Hanna

[11] 4,446,582
[45] May 8, 1984

[54] INTRA-OCULAR IMPLANT

[76] Inventor: Khalil Hanna, 5, rue Montmartre, Paris, France, 75001

[21] Appl. No.: 386,202

[22] Filed: Jun. 7, 1982

[30] Foreign Application Priority Data

Jun. 16, 1981 [FR] France ................. 81 11842

[51] Int. Cl.³ .................... A61F 1/16; A61F 1/24
[52] U.S. Cl. ................................................ 3/13
[58] Field of Search ................................. 3/13, 1

[56] References Cited

U.S. PATENT DOCUMENTS

| | | | |
|---|---|---|---|
| 3,979,780 | 9/1976 | Boniuk | 3/13 |
| 3,996,627 | 12/1976 | Deeg et al. | 3/13 |
| 4,073,015 | 2/1978 | Peyman et al. | 3/13 |
| 4,127,903 | 12/1978 | Schachar | 3/13 |
| 4,215,440 | 8/1980 | Worst | 3/13 |
| 4,242,760 | 1/1981 | Rainin | 3/13 |
| 4,285,072 | 8/1981 | Morcher et al. | 3/13 |
| 4,316,291 | 2/1982 | Severin | 3/13 |
| 4,366,582 | 1/1983 | Faulkner | 3/13 |

Primary Examiner—Ronald L. Frinks
Attorney, Agent, or Firm—Bacon & Thomas

[57] ABSTRACT

An intra-ocular implant constituted by a lens provided with loops for fixation extending substantially radially outside the lens. According to one of the features of the invention, at least one of the front loops is constituted by two wires curved towards each other and terminated by sharp points which overlap in rest position.

11 Claims, 9 Drawing Figures

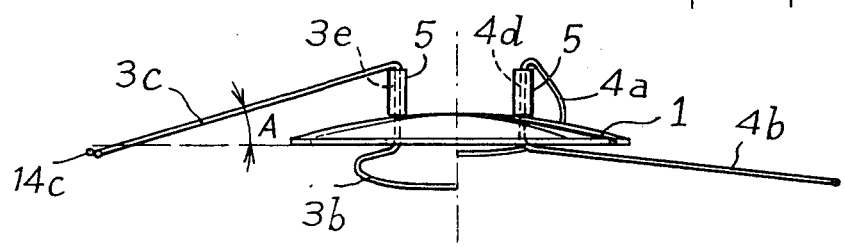
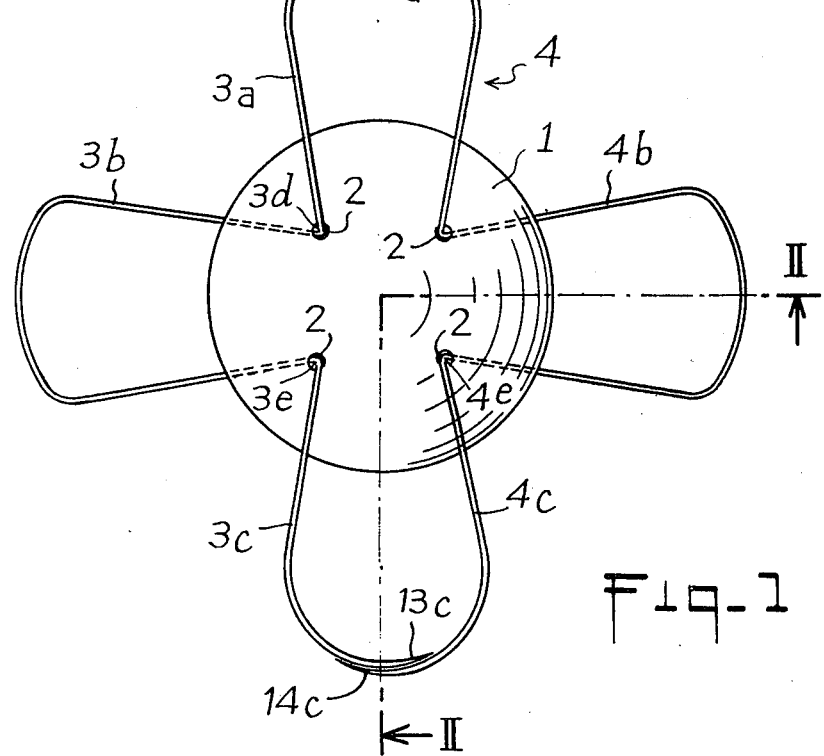

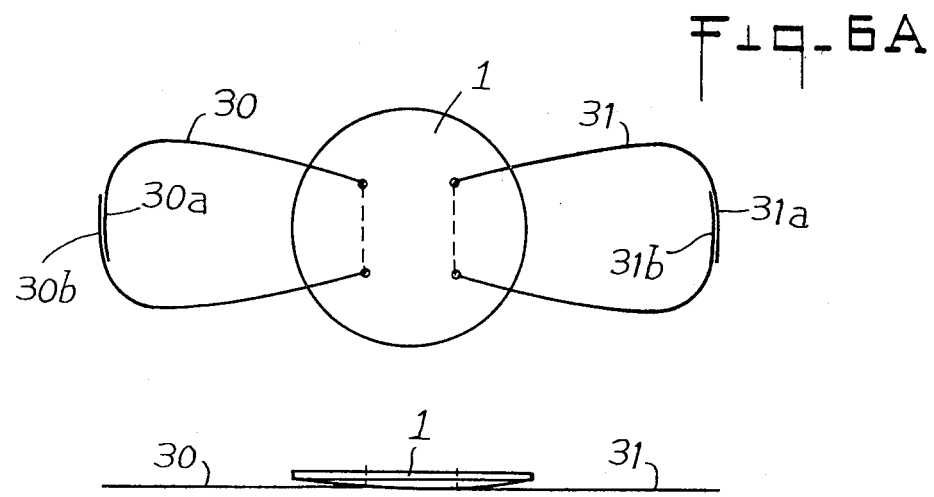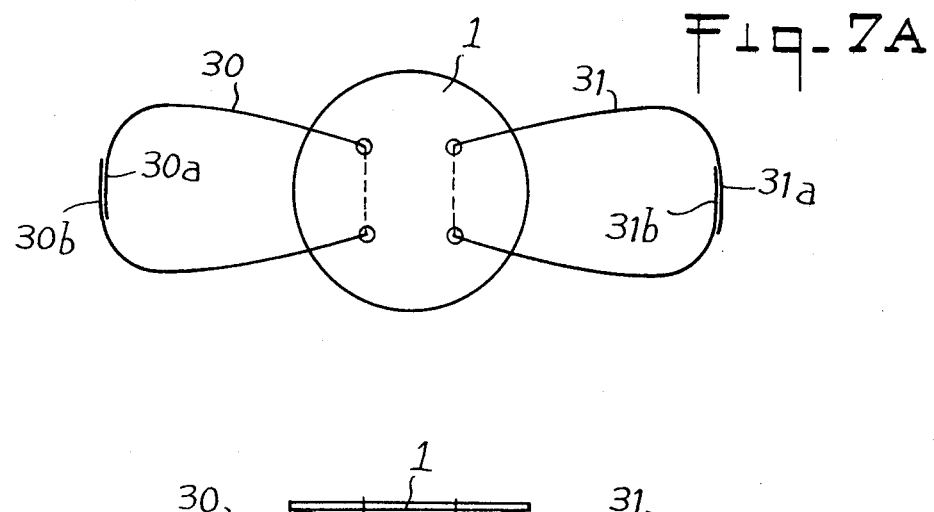

INTRA-OCULAR IMPLANT

The present invention relates to an intra-ocular implant.

Nowadays, the positioning of artificial lenses is a fairly usual procedure. Although they are now satisfactory, the solutions of fixing and holding the lenses in place in the eye still leave room for improvement. Lenses will be mentioned which are held in the eye by means of supple, slightly elastic loops abutting either in the angles of the anterior and posterior chambers of the eye according as the lens is placed in the corresponding chamber, or on the iris proper which is slightly gripped between the angularly offset front and rear loops. One of the major drawbacks of this type of fixation lies in the risks of dislocation of the implant during movements of the iris and prevents any dilation of the pupil with a view to observing the retina. In addition, the mechanical stress imposed by these loops on the tissues with which they are in contact provokes discomfort, an irritation, and even a traumatism at tissue level which leads either to intolerance or to complications and must either be constantly treated with drugs, or must be surgically operated. A recent method of implantation of this type of artificial lens consists in suturing one or two of the loops to the iris in order to avoid dislocation when the pupil dilates and thus to allow a retinal examination. Such a suture demands much skill, experience and know-how of the surgeon.

It is an object of the present invention to provide practitioners with an implant which is easy to position and of simple design, so that its manipulation is as easy as possible both from the standpoint of sterilization by heat and in operative practice.

To this end, the intra-ocular implant according to the invention is constituted by a glass lens and by at least one pair of front loops for fixation thereof, starting substantially radially from the lens, each of said loops being constituted by a filiform element.

According to one of the features of the invention, said loop is constituted by two portions of elastic wire curved towards each other in their final portion, so that their ends overlap in rest position to form a closed loop, the ends of said final portions being cut to sharp points.

In addition, each portion of elastic wire, mentioned above, of a front loop is constituted by one of the terminal portions of a continuous wire pasing through the lens and forming a rear loop, the other terminal portion of the wire also passing through the lens to constitute a portion of elastic wire of the other front loop.

The lens may comprises two, three or four orifices for passage of said wires.

Finally, said wires are bent so as to pass through the lens perpendicularly, the portions of wires thus oriented being provided, in front of or behind the lens, with spacer elements whose thickness or diameter is greater than that of the said wires or orifices.

The invention will be more readily understood on reading the following description with reference to the accompanying drawings, in which:

FIGS. 1 and 2 respectively are views in plan and section along line II—II of FIG. 1 of an embodiment of an implant according to the invention.

FIG. 3 schematically illustrates the implantation in the eye of the device of FIGS. 1 and 2.

FIGS. 6A, 6B, 7A and 7B illustrate two other variant embodiments of the invention.

Figure 3:
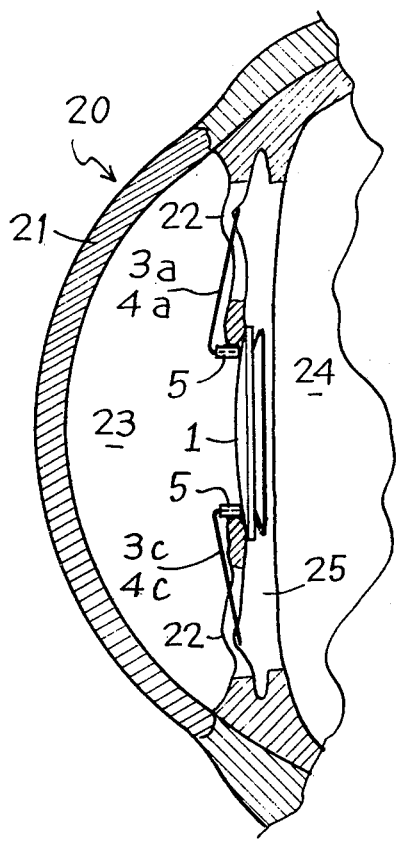

Referring now to the drawings, FIGS. 1 and 2 show an implant according to the invention, constituted by a plano-convex glass lens 1 in which four orifices 2 have been made. A first filiform element 3 is passed into two of said orifices 2 to form a front half-loop 3a, a rear loop 3b and a front half-loop 3c. Similarly, a second filiform element 4 forms a front half-loop 4a, a rear loop 4b and a front half-loop 4c. This element 3 or 4 is made of an elastic material, for example titanium, so that the loops that it forms are supple and elastically deformable. It will be noted that the final portions 3a, 3c, 4a, 4c which define the front loops for fixing the implant are curved towards each other (3a towards 4a and 3c towards 4c), so that, in rest position, their ends overlap and constitute a closed loop. In addition, these ends 13a, 13c and 14a, 14c are sharpened to sharp points.

Furthermore, it will be noted that the front portions, located in front of the lens 1, of each of the wires 3 and 4, are connected in one piece to the rear portions, behind the lens, by means of portions of wire, partly housed in the orifices 2, perpendicular to the plane of the lens. Each of these portions 3d, 3e for wire 3 and 4d, 4e for wire 4 is sufficiently long to be able to comprise, outside the orifices 2, a spacer element 5. The latter, whose diameter is greater than that of the wire or of the orifices 2, may be located, as shown in FIG. 2, in front of the lens or, on the contrary, behind it. Finally, it will be noted that the rear loops 3b, 4b are substantially parallel to the plane of the lens 1, whilst the front loops 3a, 4a and 3c, 4c form with this plane an angle A of between 10° and 20° and, preferably, 15°.

FIG. 3 schematically illustrates the implant according to the invention positioned in the eye. The eye 20 comprises, in particular, a cornea 21 defining with the iris 22 an anterior chamber 23. Behind the iris 22, but in front of the vitreous humour 24, there is a so-called posterior chamber 25. Positioning of the artificial lens of the invention requires the normal surgical manipulations of incision of the cornea and extraction of the diseased lens. The implant is then inserted by laterally sliding the rear loops 3b, 4b behind the iris by a lateral to and fro movement which is relatively simple with respect to the movements necessitated by the other implants. After the corneal incision has been sutured, the fixing of the implant consists solely in moving apart the arms 3c, 4c and 3a, 4a of the front loops with the aid of very fine hooks passed between two stitches to slide therebetween a portion of iris 22 which they perforate under the effect of their natural elastic return. The loop that they form then closes behind the iris as shown in FIG. 3. In this position, no dislocation of the implant is possible even when the pupil dilates. It will be noted that the spacer elements 5 which may be in contact with the edge of the iris when the pupil is small, prevent an effect of sawing of the iris by the wires 3 and 4. FIG. 3 shows a positioning of the implant in the posterior chamber 25 of the eye, the spacer elements 5 then being placed in front of the lens 1. On the contrary, if these spacers are placed behind the lens, the iris also evolves behind the lens and the implant is placed in the anterior chamber. In any case, whatever the chamber receiving the implant, the latter is always placed in the pupillary area, which is an ideal disposition for such a prosthesis.

The essential means of the invention, namely at least one front loop divided into two portions elastically returned towards each other and overlapping and having sharp points, may be used in any known prosthesis having filiform loops made of metal or synthetic material. They may also be applied to lenses made of synthetic material. However, it is preferable, for reasons of sterilization, stability in time and tolerance by the organism, to adopt a glass lens and loops made of metal such as titanium or other inert material.

The implant according to the invention eliminates any suture and particularly the lower suture which is a delicate operation. It also considerably reduces the duration of the operation.

A further advantage of the implant according to the invention will also be noted. For a lens disposed in the posterior chamber, the front loops constitute points of abutment in the event of effacement of the anterior chamber. The contact surface of the endothelium with the prosthesis is consequently extremely reduced and such effacement does not lead to damaging the majority of the endothelial cells as is the case with known prostheses with fixation to the iris.

Figure 4:
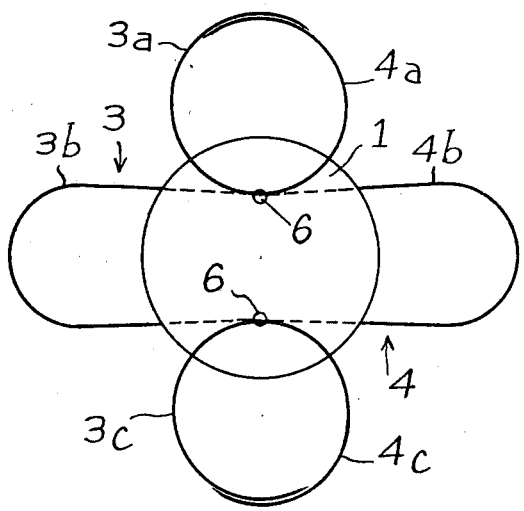
FIGS. 4 and 5 illustrate two variants of the implant according to the invention.
Figure 5:
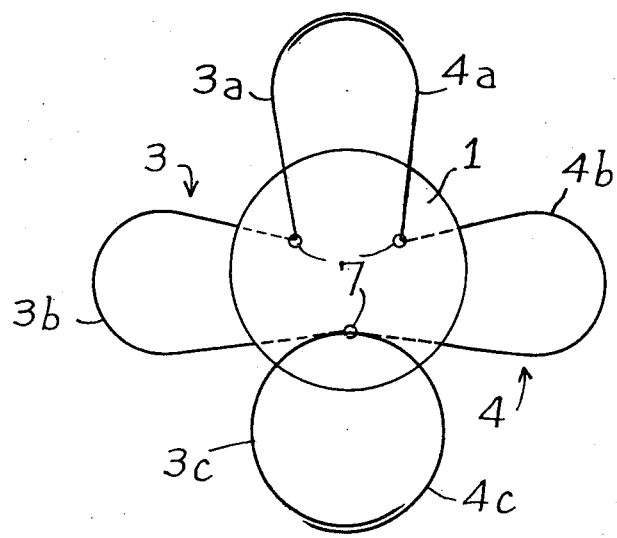

FIGS. 4 and 5 show variant embodiments of the implant according to the invention. In FIG. 4, the lens 1 possesses only two orifices through which pass the two wires 3 and 4 forming the fixing loops. The lens 1 of FIG. 5 comprises only three orifices 7, the lower orifice having the two wires 3 and 4 passing therethrough. It will be noted that, as in the preceding case, two laterally disposed rear loops will have been retained to facilitate positioning thereof behind the iris.

The spacers 5 may either be in one piece with the wire 3 or 4, or added thereto. In the latter case, they will be constituted by a section of tube of polished titanium, substantially half a millimeter high, which will be deformed along its generatrix facing the centre of the lens to grip the portion of wire 3d, 3e, 4d, 4e on which it is placed. The diameter of this tube may be of the order of 0.2 mm on the outside and 0.1 mm on the inside.

The dimensional characteristics of the implant according to the invention in all its variants will be indicated hereinafter by way of example:

lens:
　diameter: 4 mm
　thickness at the edge: 0.03 mm
　thickness at the centre: 0.173 mm
　material: glass
　power: 19 diopters
　volume: 1.273 mm$^3$
　weight in air: 3.565 mg
　refractive index: 1.6056
loops: titanium wire of diameter: 0.05 mm
total diameter of the implant: 8.5 to 9 mm
total weight in water: 2.497 mg FIGS. 6A, 6B and 7A, 7B show a lens 1 which comprises only two loops 30 and 31. These loops are substantially radial and diametrically opposite each other and, as in the preceding variants, are constituted by curved titanium-alloy wires terminated by sharp points 30a, 30b, 31a, 31b which overlap. In the case of FIGS. 6A and 6B, the loops are substantially in the plane of the lens. In the case of FIGS. 7A and 7B, tubular spacers 5 are provided, as in the preceding Figures.

The above two variants offer the advantage of being able to be implanted in secondary manner, i.e. on an eye which has already been operated on for cataract (especially if the latter is unilateral) and which has not tolerated a corneal lens. The eye is then operated on again to position an artifical lens in order to re-establish binocular vision.

Due to the geometry of the implant according to this variant, the corneal or limbic incision necessary for positioning thereof is of small dimensions (less than five millimeters). The ends of the loops are, after fixation, located behind the iris and therefore do not touch either the cornea or the angle of the anterior chamber. The tubular spacer elements make it possible to locate the lens in the retro-iridic plane, therefore remote from the cornea and to obtain a very precise centering of the lens due to the pupil.

The version of FIGS. 6A and 6B without spacer elements is very simple to introduce as the lens and the loops are in the same plane. The largest dimensions of the implant may be from 9 to 12 mm, which is possible due to the situation of the points of the loops behind the iris and which allows a complete dilation of the pupil without deformation.

Furthermore, it should be noted that it is possible to improve the surface state of the loops and to prevent oxidation of the glass of the lens, on the one hand, and to improve the chemical inertia and therefore tolerance and stability in time of the implant according to the invention, on the other hand, by depositing a fine film of quartz on the elements constituting it. This deposit may be made before or after assembly thereof.

The invention finds advantageous application in the domain of eye surgery.

It is not limited to the description which has just been given, but covers all variants thereto which may be made without departing from the scope thereof.

What is claimed is:

1. In an intra-ocular implant forming artificial lens constituted by a glass lens and at least one pair of front loops for fixation thereof starting substantially radially from the lens, each of said loops being constituted by a filiform element, said loop is constituted by two portions of elastic wire curved towards each other in their final portion, so that their ends overlap in rest position to form a closed loop, the ends of said final portions being sharpened to sharp points.

2. The intra-ocular implant of claim 1, wherein each of the loops forms an angle of about 10° to 20° with the plane of the lens which they intersect outside said lens.

3. The implant of claim 1, wherein each portion of elastic wire of a front loop is constituted by one of the terminal portions of a continuous wire passing through the lens and forming a rear loop, the other terminal portion of the wire also passing through the lens to constitute a portion of elastic wire of the other front loop.

4. The implant of claim 3, wherein the lens comprises four orifices for passage of each of the two wires.

5. The implant of claim 3, wherein the lens comprises three orifices for passage of each of said two wires.

6. The implant of claim 3, wherein the lens comprises two orifices for passage of each of the two wires.

7. The implant of claim 3, wherein the wires are bent so as to present, at orifice level, sections substantially perpendicular to said lens.

8. The implant of claim 7, wherein the sections comprise spacer elements whose thickness is greater than the diameter of the wires or orifices.

9. The implant of claim 8, wherein the spacer elements are located in front of the lens.

10. The implant of claim 8, wherein the spacers are located behind the lens.

11. The implant of claim 1, wherein it comprises only two diametrically opposite front loops, each being formed by a wire with ends with sharp points, overlapping each other at rest.

* * * * *